(12) United States Patent
Mayr et al.

(10) Patent No.: US 12,207,982 B2
(45) Date of Patent: Jan. 28, 2025

(54) PROCESS FOR PRODUCING A SINTERED LITHIUM DISILICATE GLASS CERAMIC DENTAL RESTORATION AND KIT OF PARTS

(71) Applicant: Solventum Intellectual Properties Company, Maplewood, MN (US)

(72) Inventors: Helmar Mayr, Kaufering (DE); Gallus Schechner, Herrsching (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 17/567,323

(22) Filed: Jan. 3, 2022

(65) Prior Publication Data

US 2022/0125561 A1 Apr. 28, 2022

Related U.S. Application Data (63) Continuation of application No. 15/319,138, filed as application No. PCT/US2015/035734 on Jun. 15, 2015, now abandoned.

(30) Foreign Application Priority Data

Jun. 23, 2014 (EP) .................... 14173389

(51) Int. Cl.
*A61C 13/00* (2006.01)
*A61C 5/77* (2017.01)
(Continued)

(52) U.S. Cl.
CPC ............ *A61C 13/0006* (2013.01); *A61C 5/77* (2017.02); *A61C 13/0004* (2013.01); *A61C 13/0022* (2013.01); *A61C 13/083* (2013.01); *A61K 6/15* (2020.01); *A61K 6/16* (2020.01); *A61K 6/78* (2020.01); *A61K 6/818* (2020.01); *A61K 6/822* (2020.01); *A61K 6/853* (2020.01); *A61K 6/871* (2020.01); *B33Y 10/00* (2014.12); *B33Y 70/00* (2014.12); *B33Y 80/00* (2014.12); *C03B 19/01* (2013.01); *C03B 19/06* (2013.01); *C03C 3/097* (2013.01); *C03C 4/0021* (2013.01); *C03C 8/08* (2013.01); *C03C 10/0027* (2013.01); *C03C 17/001* (2013.01); *C03C 19/00* (2013.01); *A61C 5/70* (2017.02); *C03C 2204/00* (2013.01);
(Continued)

(58) Field of Classification Search
None
See application file for complete search history.

(56) References Cited

U.S. PATENT DOCUMENTS 5,902,441 A 5/1999 Bredt
6,322,728 B1 11/2001 Brodkin
(Continued)

FOREIGN PATENT DOCUMENTS

CA 2213390 3/1998
DE 102009060274 6/2011
(Continued)

*Primary Examiner* — Queenie S Dehghan (57) ABSTRACT

A process for producing a sintered lithium disilicate glass ceramic dental restoration by way of sintering under reduced atmospheric pressure conditions at a temperature above 600° C. is described. Further described is a kit of parts for producing a sintered lithium disilicate glass ceramic dental restoration.

14 Claims, 2 Drawing Sheets

(51) Int. Cl.

| | | |
|---|---|---|
| *A61C 13/083* | (2006.01) | |
| *A61K 6/15* | (2020.01) | |
| *A61K 6/16* | (2020.01) | |
| *A61K 6/78* | (2020.01) | |
| *A61K 6/818* | (2020.01) | |
| *A61K 6/822* | (2020.01) | |
| *A61K 6/853* | (2020.01) | |
| *A61K 6/871* | (2020.01) | |
| *B33Y 10/00* | (2015.01) | |
| *B33Y 70/00* | (2020.01) | |
| *B33Y 80/00* | (2015.01) | |
| *C03B 19/01* | (2006.01) | |
| *C03B 19/06* | (2006.01) | |
| *C03C 3/097* | (2006.01) | |
| *C03C 4/00* | (2006.01) | |
| *C03C 8/08* | (2006.01) | |
| *C03C 10/00* | (2006.01) | |
| *C03C 17/00* | (2006.01) | |
| *C03C 19/00* | (2006.01) | |
| *A61C 5/70* | (2017.01) | |

(52) U.S. Cl.
CPC .... *C03C 2205/06* (2013.01); *C03C 2217/485* (2013.01); *C03C 2218/111* (2013.01); *C03C 2218/114* (2013.01)

(56) References Cited

U.S. PATENT DOCUMENTS

| | | |
|---|---|---|
| 6,420,288 B2 | 7/2002 | Schweiger |
| 6,455,451 B1 | 9/2002 | Brodkin |
| 6,517,623 B1 | 2/2003 | Brodkin |
| 6,955,776 B1 | 10/2005 | Feenstra |
| 7,086,863 B2 * | 8/2006 | Van der Zel ............ A61C 5/77 264/20 |
| 7,452,836 B2 | 11/2008 | Apel |
| 7,816,291 B2 | 10/2010 | Schweiger |
| 8,444,756 B2 | 5/2013 | Schweiger |
| 8,557,150 B2 | 10/2013 | Ritzbeger |
| 2007/0042889 A1 | 2/2007 | Apel |
| 2009/0042717 A1 | 2/2009 | Fujimoto |
| 2009/0291820 A1 | 11/2009 | Schweiger |
| 2010/0248189 A1 | 9/2010 | Burger |
| 2011/0009254 A1 | 1/2011 | Schweiger |
| 2012/0248642 A1 | 10/2012 | Ritzberger |
| 2013/0224688 A1 | 8/2013 | Mayr |
| 2014/0070435 A1 | 3/2014 | Thiel |
| 2018/0099899 A1 | 4/2018 | Ritzberger |

FOREIGN PATENT DOCUMENTS

| | | |
|---|---|---|
| EP | 0916625 | 5/1999 |
| EP | 0827941 B1 | 11/1999 |
| EP | 2450000 | 5/2012 |
| JP | 2005-112705 | 4/2005 |
| WO | WO 2000-46168 | 8/2000 |
| WO | WO 2004-110959 | 12/2004 |
| WO | WO 2008-098157 | 8/2008 |
| WO | WO 2009-014903 | 1/2009 |
| WO | WO 2013-022612 | 2/2013 |
| WO | WO 2013-053863 | 4/2013 |
| WO | WO 2013-122662 | 8/2013 |
| WO | WO 2013-167723 | 11/2013 |
| WO | WO 2013-181262 | 12/2013 |

* cited by examiner

PROCESS FOR PRODUCING A SINTERED LITHIUM DISILICATE GLASS CERAMIC DENTAL RESTORATION AND KIT OF PARTS

CROSS REFERENCE TO RELATED APPLICATIONS

This application is a continuation of U.S. application Ser. No. 15/319,138, filed Dec. 15, 2016, which is a national stage filing under 35 U.S.C. 371 of PCT/US2015/035734, filed Jun. 15, 2015, which claims the benefit of European Application No. 14173389.9, filed Jun. 23, 2014, the disclosure of which is incorporated by reference in its/their entirety herein.

FIELD OF THE INVENTION

The invention relates to a process for producing a sintered lithium disilicate glass ceramic dental restoration out of a porous 3-dim article. The process comprises the step of sintering the porous 3-dim article having the shape of a dental restoration with an outer and inner surface to obtain a sintered lithium disilicate ceramic dental restoration.

BACKGROUND ART

Lithium disilicate glass ceramics are widely used in the dental industry since many years, because the material is said to have a sufficient strength (e.g. about 400 MPa) and good aesthetic properties (mainly high translucency) after sintering.
A dental milling block out of that material is typically provided as follows:
A powder mixture of oxide and colorants, if desired, is melted, casted into a mould, and cooled, resulting in a dense glass body.
The dense glass body is then heat treated in a first crystallization step resulting in a dense part containing lithium metasilicate as main crystalline phase. Pre-colored blocks are also available allowing the manufacturing of dental restorations in different tooth colors.
A dental article (e.g. crown) can be ground out of this block. This is typically done in a dental lab.
Due to presence of lithium metasilicate as main crystalline phase in the dental milling block, applying a dry milling process for producing a dental restoration is not possible. The respective block has to be shaped by applying a grinding process. A second heat treatment/crystallization step is needed to give the dental restoration its final optical and mechanical properties. If desired, the obtained dental restoration can be further individualized by applying e.g. a veneering material.
The current process has a limited productivity due to its restriction to wet grinding and offers only limited possibilities for the dental technician to individualize the desired dental article especially with respect to colors and their distribution.
EP 2 450 000 (3M IPC) describes the use of an open celled glass or glass ceramic article, produced by a rapid prototyping method, which is sintered on a ceramic framework. A process for producing a dental article is described comprising Part A and Part B, Part A and Part B each having a 3-dim. Structure and an outer and an inner surface, the outer surface of Part A having a shape which essentially corresponds to the shape of the inner surface of Part B, Part B comprising a material with a porous section and being produced with the aid of a rapid-prototyping technique, the process comprising a heating step, wherein Part A is serving as support structure for Part B during said heating step.
EP 0 916 625 (Ivoclar) describes a process for producing molded translucent lithium disilicate glass ceramic products, the process comprising the steps of a) providing a melt of a glass comprising certain metal oxides, b) forming an cooling the melt to a desired shape, c) tempering the formed glass-product in a range from 400 to 1100° C. to obtain a glass ceramic product. Step b) is typically conducted by applying pressure to increase the density.
US 2010/0248189 (3M IPC) describes the use of an open celled block consisting of glass or glass ceramic for use as a facing. US 2014/0070435 (Vita) describes a porous, silicate, ceramic body with a first density which can be sintered into a silicate, ceramic body with a second density mainly used as a veneering U.S. Pat. No. 6,517,623 (Jeneric/Pentron Inc.) describes the use of crystallized lithium disilicate as a pressing material. U.S. Pat. No. 8,444,756 (IvoclarVivadent) describes the use of the material as a veneering material on zirconia after being crystallized in the powder state. U.S. Pat. No. 8,557,150 (IvoclarVivadent) describes the established two step process (lithium metasilicate containing block—grinding—crystallization) for producing a lithium disilicate glass ceramic dental article. DE 19 647 739 (IvoclarVivadent) describes the use of lithium disilicate ingots.
U.S. Pat. No. 6,455,451 (Jeneric/Pentron Inc) describes various compositions for lithium disilicate glass ceramic ingots and the process for pressing dental articles. U.S. Pat. Nos. 7,452,836 and 7,816,291 (IvoclarVivadent) describe compositions and process for lithium delicate glass ceramic. DE 10 2009 060 (DeguDent, Vita Zahnfabrik, Fraunhofergesellschaft) describes different compositions for lithium disilicate glass ceramics where coloring is done in the melting process and the material is machined in the lithium metasilicate state.
WO 2013/053863 (IvoclarVivadent) describes possible compositions for lithium disilicate glass ceramics that are processed by machining in the lithium metasilicate state and subsequent crystallization.
US 2009/0042717 (Apel et al.) describes lithium silicate materials which are said to be easily millable and having a high strength. The lithium silicate materials contain Me(II)O being selected from CaO, BaO and SrO and less than 0.1 wt.-% ZnO.
U.S. Pat. No. 6,420,288 B2 (Schweiger et al.) deals with a process for the preparation of shaped translucent lithium disilicate glass ceramic products, which comprises producing a melt of a starting glass containing $SiO_2$ (57.0 to 80.0 wt.-%), $Al_2O_3$ (0 to 5.0 wt.-%), $La_2O_3$ (0.1 to 6.0 wt.-%), MgO (0 to 5.0 wt.-%), ZnO (0 to 8.0 wt.-%) and $Li_2O$ (11.0 to 19.0 wt.-%). It is mentioned that the additional incorporation of $ZrO_2$ led to an increase in translucency.
WO 2013/167723 A1 (Ivoclar) relates to pre-sintered blanks on the basis of lithium disilicate glass-ceramic which are particularly suitable for the production of dental restorations. To avoid distortion it is suggested that the sintering should be conducted using a supporting material having the same chemical composition.

DESCRIPTION OF THE INVENTION

However, there is still a desire for a simplified process for the production of dental restorations based on lithium disilicate material resulting after sintering to a highly aesthetic product. It would also be desirable to be able to produce dental restorations based on a lithium disilicate material by applying a dry milling process. It would also be desirable, to be able to produce dental restorations based on a lithium disilicate material by applying a simplified sintering process.

It would also be desirable, to be able to produce dental restorations based on a lithium disilicate material wherein the dental restorations can easily be individualized e.g. with respect to color.

The invention described in the present text solves at least some of the above needs.

According to one aspect, the invention relates to a process for producing a sintered lithium disilicate glass ceramic dental restoration out of a porous 3-dim article, the process comprising the step of     sintering the porous 3-dim article having the shape of a dental restoration with an outer and inner surface to obtain a sintered lithium disilicate ceramic dental restoration, the sintered lithium disilicate glass ceramic dental restoration comprising     Si oxide calculated as SiO2 from 55 to 80 wt.-%,
    Li oxide calculated as Li2O from 7 to 16 wt.-%,
    Al oxide calculated as Al2O3 from 1 to 5 wt.-%, and
    P oxide calculated as P2O5 from 1 to 5 wt.-%, wt.-% with respect to the weight of the dental restoration, the sintering preferably being done under reduced atmospheric pressure conditions, the reduced atmospheric pressure conditions being applied at a temperature above 600 or 700° C., but not below.

In a further aspect, the invention relates to a kit of parts comprising a porous 3-dim article having the shape of a dental milling block, and
    an instruction of use comprising the following process steps:
        machining a porous dental restoration out of the 3-dim porous article having the shape of a dental milling block,
        optionally coloring the porous dental restoration with a coloring solution,
        conducting the sintering of the porous dental restoration under reduced atmospheric pressure conditions, the reduced atmospheric pressure conditions being applied at least in a temperature range from 600 to 800° C.,
        optionally sintering the porous dental restoration without using a support structure during sintering,
    the porous 3-dim article having a pore volume from 70 to 20 vol.-% and comprising the following oxides:
        Si oxide calculated as SiO2 from 55 to 80 wt.-%,
        Li oxide calculated as Li2O from 7 to 16 wt.-%,
        Al oxide calculated as Al2O3 from 1 to 5 wt.-%, and
        P oxide calculated as P2O5 from 1 to 5 wt.-%,
wt.-% with respect to the weight of the porous 3-dim article.

Definitions

The term "3-dim dental article" means any solid article having a volume above 0.5 ml which can and is to be used in the dental field. Examples of 3-dim dental articles include dental mill blanks, dental restorations and parts thereof.

A "dental restoration" means an article to be used for restoring a missing or defective tooth structure. Dental restorations typically comprise at least two parts: a dental support structure (sometimes also referred to as frame or coping) and a dental facing. Examples of dental restorations or parts thereof include crown(s), bridge(s), veneer(s), facing(s), abutment(s), dental support structure(s), inlay(s), onlay(s), full arch prosthese(s) and monolithic structures.

The material the dental article is made of should not be detrimental to the patient's health and thus free of hazardous and toxic components being able to migrate out of the article. Dental articles are typically of small size and may comprise sections having a wall thickness in the range of about 100 μm to 2,000 μm or in the range of about 100 μm to about 500 μm. The total volume of a dental article is typically below about 100 ml or below about 50 ml or below about 10 ml or below about 5 ml. A "support structure" is to be understood as a structure being suitable to support or stabilize another article, especially during a sintering process. A "dental support structure" is to be understood as the part of a dental restoration which is typically adhered to a tooth stump or inserted into the patients mouth and suitable for being veneered by a dental facing or dental veneer. A dental support structure has typically sufficient strength to withstand chewing forces. Dental support structures are often made of or comprise polycrystalline oxide ceramic materials including $ZrO_2$, and $Al_2O_3$, metals or alloys. Compared to other framework such as pottery or paving stones, the dental framework is small and filigree and of high strength. The thickness of the dental framework can vary from very thin, e.g. at the edges and rims (below about 0.1 mm) to considerably thick, e.g. in the biting area (up to about 7 mm). However, dental frameworks may also be made of or comprise metal or metal alloys.

The term "dental facing" or "dental veneer" refers to the aesthetic part of a dental restoration, meaning the part comprising an outer surface of the finished restoration. The dental facing is further adapted to be applied to a frame or dental support structure which forms another part of the dental restoration, and the dental restoration is in turn applied to a tooth. The dental facing is preferably arranged at those parts of the dental support structure that are likely to be visible in a patient's mouth, or that in particular functionally co-operate with the adjacent or opposed teeth of a patient, for example. Dental veneers are also small and filigree objects. The strength of dental veneers, however, is typically lower compared to dental frameworks. Dental veneers are typically made of or comprise glass or glass ceramic materials.

A dental support structure or a dental veneer usually has a 3-dimensional inner and outer surface including convex and concave structures. The outer surface of the dental framework typically corresponds essentially to the inner surface of the dental veneer. The inner surface of the dental framework typically corresponds essentially to the outer surface of a prepared tooth stump, whereas the outer surface of the dental veneer typically corresponds essentially to the final dental restoration.

By "dental milling block" is meant a solid block (3-dim article) of material from which a dental article can be machined. A dental milling block may have a size of about 20 mm to about 30 mm in two dimensions, for example may have a diameter in that range, and may be of a certain length in a third dimension. A block for making a single crown may have a length of about 15 mm to about 30 mm, and a blank for making bridges may have a length of about 40 mm to about 80 mm. A typical size of a block as it is used for making a single crown has a diameter of about 24 mm and a length of about 19 mm. Further, a typical size of a block as it is used for making bridges has a diameter of about 24 mm and a length of about 58 mm. Besides the above mentioned dimensions, a dental milling block may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of about 100 to about 200 mm, with a thickness being in the range of about 10 to about 30 mm.

An "ingot" means a block of material which can be melted. Such a block is typically used in a so-called "hot pressing technique". The ingot, which is usually embedded in an investment material, is heated to a certain temperature and the material converted into a viscous state. The viscous material is applied/pressed to the desired shape of a dental article or on the outer surface of a support structure. A "powder" means a dry, bulk solid composed of a large number of very fine particles that may flow freely when shaken or tilted. A "particle" means a substance being a solid having a shape which can be geometrically determined. The shape can be regular or irregular. Particles can typically be analysed with respect to e.g. grain size and grain size distribution.

"Glass" means an inorganic non-metallic amorphous material. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. Glasses usually show an amorphous or diffuse X-ray pattern or diffraction. "Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and crystalline ceramics. Usually, it is formed as a glass, and then made to crystallize partly by heat treatment. So, glass ceramics are made of a glassy phase with crystals, which typically have no pores in the glassy phase or between crystals. Glass ceramics can mainly refer to a mixture of lithium-, silicium-, and aluminium-oxides. "Ceramic" means an inorganic non-metallic material that is produced by application of heat. Ceramics are usually hard and brittle and, in contrast to glasses or glass ceramics, display an essentially purely crystalline structure. A "ceramic article" is to be understood as an article comprising a ceramic, glass or glass ceramic material.

A "lithium silicate glass ceramic" means a material comprising quartz, lithium dioxide, phosphorous oxide and alumina. A lithium silicate glass ceramic may comprise lithium metasilicate crystals ($Li_2SiO_3$), lithium disilicate crystals ($Li_2Si_2O_5$) or a mixture of both crystals. Lithium silicate glass ceramic comprising mainly lithium metasilicate crystals has typically a low strength and toughness compared to lithium silicate glass ceramic comprising mainly lithium disilicate crystals. Lithium silicate glass ceramic comprising mainly lithium metasilicate crystals can typically be machined easily. After a machining step, the material can be converted into a lithium disilicate glass ceramic material by a heating step.

A "lithium disilicate glass ceramic" means a material comprising mainly lithium disilicate crystals (e.g. content of crystalline lithium disilicate phase above about 50 or above about 55 or above about 60 or above about 65 vol.-%; typical ranges include from about 50 to about 90 or from about 55 to about 85 or from about 60 to about 80 vol.-%).

The chemical composition of glasses, ceramics and glass ceramic compositions is typically given by referring to the respective oxides, e.g. $SiO_2$, $Li_2O$, etc.

"Density" means the ratio of mass to volume of an object. The unit of density is typically $g/cm^3$. The density of an object can be calculated e.g. by determining its volume (e.g. by calculation or applying the Archimedes principle or method) and measuring its mass. The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases. Typical values for an "open-celled" material are between about 15% and about 75% or between about 18% and about 75%, or between about 30% and about 70%, or between about 34% and about 67%, or between about 40% to about 68%, or between about 42% and about 67%. The term "closed-celled" relates to a "closed porosity". Closed cells are those cells which are not accessible from the outside and cannot be infiltrated by gases under ambient conditions. The "average connected pore diameter" means the average size of the open-celled pores of a material. The average connected pore diameter can be calculated as described in the Examples section.

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than about +/−5% or +/−2% or +/−1%.

A "solution" shall mean a composition containing solvent with soluble components dissolved therein. The solution is a liquid at ambient conditions. A "solvent" is any solvent which is able to dissolve the coloring agent. The solvent should be sufficiently chemically stable if combined with the coloring agent. That is, the solvent shall not be decomposed by the other components present in the composition.

"Soluble" means that a component (solid) can be completely dissolved within a solvent. That is, the substance is able to form individual molecules (like glucose) or ions (like sodium cations or chloride anions) when dispersed in water at 23° C. The solution process, however, might take some time, e.g. stirring the composition over a couple of hours (e.g. 10 or 20 h) might be required.

"Coloring ions" shall mean ions which have an absorption in the spectrum visible to the human eye (e.g. from about 380 to about 780 nm), which results in a colored solution (visible to the human eye), if the coloring ions are dissolved in water (e.g. about 0.6 mol/l) and/or cause a coloring effect in the article which has been treated with the coloring solution and sintered afterwards.

By "machining" is meant milling, grinding, cutting, carving, or shaping a material by a machine. Milling is usually faster and more cost effective than grinding. "Additive manufacturing" or "Build-up technology" means rapid-prototyping techniques which can be used for producing 3-dim. articles by processes including ink-jet printing, 3d-printing/ powder bed printing, multijet plotting, robo-casting, fused deposition modelling, laminated object manufacturing, selective laser sintering or melting, stereolithography, photostereolithography, or combinations thereof.

Those and other techniques are e.g. described in U.S. Pat. No. 5,902,441 (Bredt et al.), U.S. Pat. No. 6,322,728 (Brodkin et al.) and U.S. Pat. No. 6,955,776 (Feenstra) and U.S. Pat. No. 7,086,863 (Van der Zel). The disclosure of these patents as it regards the description of rapid-prototyping techniques is herewith incorporated by reference and regarded as part of this application.

Commercially available examples of rapid-prototyping equipment which can be used include printers from ZCorp. company like the printer ZPrinter™ 310 plus.

"Reduced atmospheric pressure conditions" means conditions where the atmospheric pressure is willfully lowered by applying technical means like a vacuum pump.

A composition is "essentially or substantially free of" a certain component within the meaning of the invention, if the composition does not contain said component as an essential feature. Thus, said component is not wilfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all. However, sometimes the presence of a small amount of the said component is not avoidable e.g. due to impurities.

As used herein, "a" "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about", especially if single values are concerned.

DETAILED DESCRIPTION

The process described in the present text is advantageous in a number of aspects:

It was found that highly aesthetic dental restorations based lithium disilicate material can be obtained, when during a certain temperature range the sintering is conducted under reduced atmospheric pressure conditions.

Applying the reduced atmospheric pressure conditions during a temperature range which is too low, the desired translucency of the resulting dental restoration cannot be obtained.

Further, if desired, the porous 3-dim article can easily be individualized in an early stage, e.g. by applying a coloring solution to its absorbing surface. As the 3-dim article is in a porous stage, it can also be machined easily, e.g. by using a dry milling process. In addition, the final dental restoration can be obtained in a one-step sintering process. There is no need to isolate a product having lithium metasilicate as main crystalline phase.

In contrast to the process described in EP 2 450 000 (3M IPC), there is also no need to support the inner surface of the dental restoration during sintering. It has been found that the porous dental restoration described in the present text is self-supporting during sintering. Thus, the porous 3-dim article can be sintered to its final stage without distortion of its geometry during sintering.

It was found, that in particular those dental restorations were suitable to be sintered without support during the sintering step, which were obtained from porous 3-dim articles having been manufactured by using a build-up technology.

Previously, the veneering of e.g. a zirconia dental support structure with a facing out of lithium disilicate material was either done by applying a hot-pressing technique or by grinding the veneer out of a solid dental milling block containing lithium metasilicate as main crystalline phase and conducting a crystallizing step. The process described in the present text simplifies this procedure to a great extend.

The dental restoration (e.g. veneer) can now be machined (e.g. milled) out of a pre-sintered and thus porous milling block in an efficient way and sintered to its final shape without supporting the dental restoration during sintering.

Further, according to the process described in the present text it is now possible to provide the porous 3-dim article in different shapes. The shape is not restricted by the available pressing equipment. Any shape which can be obtained by applying a build-up technology is now possible.

It was also found that conducting the sintering under reduced atmospheric pressure can be beneficial for obtaining a self-supporting 3-dim porous article, in particular a 3-dim porous article having the shape of a dental crown, dental bridge, veneer, inlay, onlay or part thereof and is advantageous for the translucency and the color.

The invention relates to a process for producing a sintered lithium disilicate glass ceramic dental restoration.

The process comprises the step of sintering a porous 3-dim article having the shape of a dental restoration with an outer and inner surface without using a support structure during the sintering process, i.e. support less. The sintering is done under reduced atmospheric pressure, in particular during a temperature range from 600 to 800° C. After sintering a sintered lithium disilicate ceramic dental restoration is obtained.

According to a further embodiment, the process comprises the steps of
  providing a porous 3-dim article, the 3-dim dental article having either the shape of a dental milling block or of a dental restoration with an outer and inner surface,
  for porous 3-dim articles having the shape of a milling block, machining the porous 3-dim article to obtain a machined porous 3-dim article having the shape of a dental restoration with an outer and inner surface,
  sintering the porous 3-dim article having the shape of a dental restoration with an outer and inner surface to obtain a sintered lithium disilicate glass ceramic dental restoration.

Thus, according to one embodiment, the porous 3-dim article has the shape of a dental milling block. According to another embodiment, the porous 3-dim article has the shape of a dental restoration with an outer and inner surface. In any case, the sintering step is applied to a porous 3-dim article having the shape of a dental restoration with an outer and inner surface, but not the 3-dim article in the shape of a dental milling block.

The porous 3-dim article can be characterized by one or more or all of the following parameters:
  Pore volume: from 20 to 70%
  Density: from 0.5 to 2 g/cm3,
  Flexural strength: from 20 to 75 MPa or from 30 to 60 MPa according to ISO 6872.
If desired, the parameters can be measured as described in the Example section below.
The porous 3-dim article comprises the same oxides as the sintered lithium disilicate ceramic article.

The porous 3-dim article can be provided by using different technologies. According to one embodiment, the porous 3-dim article is provided by using an additive manufacturing technology. Suitable additive manufacturing technologies are given in the definition section above. Using an additive manufacturing technology allows the manufacturing of basically any desired shape of the porous 3-dim article. Using an additive manufacturing technology also allows the manufacturing of fully or only partially colored porous 3-dim articles.

In particular, using an additive manufacturing technology allows the manufacturing of a porous 3-dim article having the shape of a dental restoration and containing coloring components (e.g. ions or pigments), which after sintering result in a tooth-colored dental restoration.

The coloring components can be applied in liquid or solid form during the additive manufacturing process. Suitable coloring components include those as described for the coloring solutions in the text further down below.

If desired, a heating or pre-sintering step can be applied to strengthen the structure of the porous 3-dim article. According to one embodiment, the build-up technology makes use of a glass powder. The particles in the glass powder typically have a particle size below about 70 μm or below about 60 μm or below about 25 μm. If desired, the particle size can be measured with laser diffraction. The adjustment of the particle size can be done using a sieve having the desired maximum mesh size.

If larger particles are used for producing the article (e.g. particles having a particle diameter above about 70 μm or above about 80 μm), the surface resolution of the final product might be reduced.

The nature and structure of the glass powder is not particularly limited unless it is detrimental to the desired performance of the composition.

The glass powder is preferably selected to be compatible for use in human bodies. Furthermore, the glass powder is preferably selected to provide good aesthetic appearance for the dental restoration, in particular when combined with a dental framework.

Glass powder which can be used can typically be characterized by at least one of the following features:
  comprising:
    Si oxide calculated as SiO2: from 55 to 80 wt.-%, or from 59 to 72 wt.-%;
    Li oxide calculated as Li2O: from 7 to 20 wt.-%, or from 10 to 16 wt.-%;
    Al oxide calculated as Al2O3: from 1 to 5 wt.-%;
    P oxide calculated as P2O5: from 1 to 5 wt.-%;
  coefficient of thermal expansion: about $8*10^{-6}K^{-1}$ to about $15.8*10^{-6}K^{-1}$ or $8*10^{-6}K^{-1}$ to about $9*10^{-6}K^{-1}$ or about $12*10^{-6}K^{-1}$ to about $13.6*10^{-6}K^{-1}$ or from about $15*10^{-6}K^{-1}$ to $15.8*10^{-6}K^{-1}$;
  melting temperature (range): around or less than about 1000° C.;
  density: about 2.0 to about 3.0 or about 2.2 to about 2.6 g/cm$^3$ and/or
  glass transition temperature: 500 to 600° C. or 520 to 580° C., preferably about 550° C.

According to another embodiment, the porous 3-dim article is provided by using a technology comprising a pressing step and heating step or pre-sintering step. According to this embodiment, a glass powder is provided first and pressed to a 3-dim article (sometimes also referred to as "green body").

In a further step, the 3-dim article is heated or pre-sintered to obtain a porous 3-dim article (sometimes also referred to as "white body").

The temperature is adjusted to a range so that the porous 3-dim article does not contain lithium metasilicate or lithium disilicate as main crystalline phase. Instead, the 3-dim article is mainly still in an amorphous state.

Suitable pressure ranges for the pressing step include: from 0.1 to 20 MPa or from 0.5 to 15 MPa or from 1 to 10 MPa.

Suitable temperature ranges for the heating or pre-sintering step include: from 400 to 700° C. or from 450 to 650° C. or from 500 to 600° C.

The sintering of the porous 3-dim article having the shape of a dental restoration is typically conducted within a temperature range from 800 to 1000° C. or from 850 to 975° C. or from 900 to 950° C.

It was found that conducting the sintering under reduced atmospheric pressure is beneficial, in particular, if a self-supporting porous 3-dim article and a high translucent and tooth colored restoration is desired.

Without wishing to be bound to a certain theory, it is assumed that reducing the atmospheric pressure during sintering may help to reducing the number of voids which may be present in the sintered article "Reduced atmospheric pressure" means that the pressure is at least 80% or at least 90% or at least 95% below the ambient conditions.

Suitable conditions include the following ranges: from 200 to 5 hPa or from 100 to 10 hPa or from 50 to 25 hPa.

Applying reduced pressure only during certain time and/or temperature regimes during sintering may also help to reduce or avoid the formation of higher porosities, improves the translucency, may help to reach the desired coloration, and may help to reduce the overall sintering time.

It can be preferred, if the reduced atmospheric pressure conditions are applied not from the beginning of the sintering process, but later, e.g. after having conducted a first heat treatment.

It can also be preferred, if the reduced atmospheric pressure conditions are applied not until end of the cooling down period, but stopped at the temperature obtained by conducting the first heat treatment.

According to one embodiment, the sintering process is conducted as follows:
Conducting a first heat treatment to obtain a first temperature T1 at an atmospheric pressure P1, T1 being preferably in the range of 600 to 800° C. or 700 to 800° C., P1 being in the range of 900 to 1100 hPa,
Holding temperature T1 and applying reduced atmospheric pressure conditions P2, P2 being preferably in the range of 20 to 50 hPa,
Conducting a second heat treatment to obtain a second temperature T2, T2 being preferably in the range of 850 to 1,000° C.,
Holding at that temperature T2 for a defined time t, t being preferably in the range of 180 to 1,800 s,
Conducting a first cooling treatment until T1 is reached,
Increasing the atmospheric pressure until P1 is reached,
Conducting a second cooling treatment until room temperature (e.g. 23° C.) is reached.

At the end of the sintering step a sintered litihium disilicate glass ceramic dental article in the shape of a dental restoration is obtained. That is, the obtained dental restoration comprises lithium disilicate as main crystal phase (i.e. more than 50 vol.-%).

The sintering of the porous 3-dim article having the shape of a dental restoration is typically done without supporting the inner surface of the dental restoration during sintering.

This is a great benefit compared to other processes described in the art, which typically require that at least the inner surface of the porous dental restoration is supported during sintering to avoid distortion, e.g. as described in US 2013 224688 (3M IPC).

In that document, the outer surface of the corresponding support structure is used to support the inner surface of the porous dental restoration.

Likewise, WO 2013/167723 A1 suggests conducting the sintering step by supporting the article to be sintered.

During sintering, the material of the porous 3-dim article having the shape of a dental restoration undergoes a sintering and a crystallization process with the result that at the end the material contains lithium disilicate as main crystalline phase (i.e. above 50 vol.-%).

The obtained sintered lithium silicate glass ceramic material may fulfill at least one or more or all of the following parameters:
Translucency: from 0.03 to 0.60 or from 0.1 to 0.4 (Mac Beth TD 932 sample thickness 1.50+/−0.05 mm polished with 9 μm sandpaper); a translucency of 0.0 means that the sample is fully transparent.
Radiopacity: of more than 200%, or more than 300% (according to ISO 6872);
Coefficient of thermal expansion: from 8.0 to $12*10^{-6}$/K or from 8.0 to $11*10^{-6}$/K or from 9.0 to $10.4*10^{-6}$/K (according to ISO 6872);
Vickers hardness: at least 500 or at least 520 or at least 550 (HV; 0.2 kg);
Flexural strength: of at least 250 MPa or at least 350 or at least 400 (according to ISO 6872);
Refractive index: in the range of 1.545 to 1.525 or in the range of 1.530 to 1.540 (measured with an Abee Refractometer).

If desired, the respective parameters can be determined as outlined in the example section below.

The sintered lithium disilicate glass ceramic material is characterized by comprising the following components:
Si oxide calculated as SiO2: from 55 to 80 wt.-%, or from 59 to 72 wt.-%;
Li oxide calculated as Li2O: from 7 to 20 wt.-%, or from 10 to 16 wt.-%;
Al oxide calculated as Al2O3: from 1 to 5 wt.-%;
P oxide calculated as P2O5: from 1 to 5 wt.-%.

The sintered lithium disilicate glass ceramic may further comprise:
K oxide calculated as K2O from 0 to 0.1 wt.-% or from 0.001 to 0.002 wt.-%;
Zr oxide calculated as ZrO2 from 0.0 to 4.0 wt.-% or from 0.01 to 0.05 wt.-%;
Zn oxide calculated as ZnO from 0 to 0.2 wt.-% or from 0.002 to 0.01 wt.-%;
Ce oxide calculated as CeO2 from 0.0 to 3.0 wt.-% or from 0.1 to 2.0 wt.-%;
Cs oxide calculated as Cs2O from 6 to 30 wt.-% or from 10 to 15 wt.-%;
Coloring components calculated as the respective oxides: from 0 to 10 wt.-% or from 0.25 to 8 wt.-% or from 0.5 to 6 wt.-%.

Suitable coloring oxides comprise the oxides of V, Mn, Fe, Er, Tb, Y, Ce, Sm, Dy and mixtures thereof.

The lithium disilicate glass ceramic material does typically not comprise Zr oxide calculated as ZrO2: more than 20 wt.-%, more than 15 wt.-% or more than 12 wt.-%.

According to another embodiment, the sintered lithium disilicate glass ceramic material may have the following composition, wherein the content of the various ions is calculated based on the respective oxide:
Si oxide calculated as SiO2 from 55 to 80 wt.-% or from 60 to 65 wt.-%,
Al oxide calculated as Al2O3 from 1 to 5 wt.-% or from 1 to 2 wt.-%, B oxide calculated as B2O3 from 0 to 5 wt.-% or from 0 to 2 wt.-%, Li oxide calculated as Li2O from 7 to 16 wt.-% or from 8 to 13 wt.-%, Na oxide calculated as Na2O from 0 to 1 wt.-% or from 0.05 to 0.2 wt.-%, Cs oxide calculated as Cs2O from 6 to 30 wt.-% or from 10 to 15 wt.-%, P oxide calculated as P2O5 from 1 to 5 wt.-% or from 1.5 to 3.0 wt.-%.

According to a further embodiment, the following components might be present either alone or in combination with others.

Sr oxide calculated as SrO from 0.0 to 5 wt.-% or from 0.1 to 3.0 wt.-%;

Ba oxide calculated as BaO from 0.0 to 7 wt.-% or from 0.1 to 3.0 wt.-%;

Ti oxide calculated as TiO2 from 0.0 to 2 wt.-% or from 0.1 to 3.0 wt.-%;

Zr oxide calculated as ZrO2 from 0.0 to 4.0 wt.-% or from 0.01 to 0.05 wt.-%;

Hf oxide calculated as HfO2 from 0.0 to 5.0 wt.-% or from 2.0 to 4.0 wt.-%;

Fe oxide calculated as Fe2O3 from 0.0 to 0.5 wt.-% or from 0.1 to 0.3 wt.-%;

V oxide calculated as VO2 from 0.0 to 0.5 wt.-% or from 0.01 to 0.3 wt.-%;

Y oxide calculated as Y2O3 from 0.0 to 1.5 wt.-% or from 0.1 to 1.0 wt.-%;

Ce oxide calculated as CeO2 from 0.0 to 3.0 wt.-% or from 0.1 to 2.0 wt.-%;

Sm oxide calculated as Sm2O3 from 0.0 to 2.0 wt.-% or from 0.0 to 1.0 wt.-%;

Er oxide calculated as Er2O3 from 0.0 to 2.0 wt.-% or from 0.01 to 0.4 wt.-%;

Dy oxide calculated as Dy2O3 from 0 to 1.0 wt.-% or from 0.1 to 0.2 wt.-%;

K oxide calculated as K2O from 0 to 0.1 wt.-% or from 0.001 to 0.002 wt.-%;

Mg oxide calculated as MgO from 0 to 0.2 wt.-% or from 0.002 to 0.01 wt.-%;

Zn oxide calculated as ZnO from 0 to 0.2 wt.-% or from 0.002 to 0.01 wt.-%;

La oxide calculated as La2O3 from 0 to 0.1 wt.-% or from about 0.0001 to 0.01 wt.-%;

wt.-% with respect to the weight of the lithium silicate glass ceramic.

Certain of these oxides may fulfill specific functions during the production process:

SiO2 may function as a network former and lithium silicate precursor.

Al2O3 may increase the chemical stability of the glass matrix.

Li2O may act as lithium silicate precursor.

Cs2O may function as fluxing agent and may help to control the phase separation and increase the radiopacity.

P2O5 may function as nucleating agent.

CeO2 may act as oxidative coloring stabilizer.

Er2O3 may act as a color adjusting agent (e.g. to reduce the greenish color fault).

BaO, SrO, Y2O3, ZrO2 and HfO2 can be used to adjust the refractive index of the glass matrix.

The inventive lithium silicate glass ceramic does typically not comprise K2O, MgO, ZnO, La2O3 or a mixture of those in an amount above 0.5 wt.-% or above 0.4 wt.-% or above 0.3 wt.-% or above 0.2 wt. % or above 0.1 wt.-% with respect to the weight of the ceramic.

According to a particular embodiment, the lithium silicate glass ceramic does not comprise K2O in an amount 0.4 wt.-% or above 0.3 wt.-% or above 0.2 wt.-% or above 0.1 wt.-% with respect to the weight of the ceramic.

The Li2O content is typically below 17 wt.-% or below 16 wt.-% with respect to the weight of the glass ceramic.

Reducing the amount of either of oxides K2O, MgO, ZnO, La2O3 may facilitate the production of a translucent ceramic material having the desired CTE value.

The lithium disilicate glass ceramic material described in the present text does typically not comprise either of the following crystal phases in an amount above 50 or above 40 or above 30 or above 20 or above 10 or above 5% (at room ambient conditions; e.g. 23° C.): apatite, tetragonal or cubic leucit, If desired, the porous 3-dim article in the shape of a dental restoration can be colored using a suitable coloring solution.

According to one embodiment, the coloring solution is used for being selectively applied to parts of the surface of the porous 3-dim article. That is, the solution is only applied to parts of the surface of the 3-dim article but not to the whole surface.

According to another embodiment the solution is used for being applied to the whole surface of the porous 3-dim article. This can be achieved, e.g. by dipping the article completely into the coloring solution.

The porous 3-dim article is usually treated with the solution for about 0.5 to about 5 minutes, preferably from about 1 to about 3 minutes at room temperature (about 23° C.). Preferably no pressure is used. A penetration depth of the solution into the article of about 5 mm is considered to be sufficient.

If a coloring solution is used, the process of producing the dental restoration comprises the following steps:

providing a porous 3-dim article, the 3-dim article having either the shape of a dental milling block or of a dental restoration with an outer and inner surface, for porous 3-dim articles having the shape of a milling block, machining the porous 3-dim article to obtain a machined porous 3-dim article having the shape of a dental restoration with an outer and inner surface applying a coloring solution as described in the present text to the surface of the porous 3-dim article, optionally drying the porous 3-dim article to which the coloring solution has been applied, sintering the porous 3-dim article having the shape of a dental restoration with an outer and inner surface to obtain an at least partially colored and sintered lithium disilicate ceramic dental restoration.

Coloring solutions which can be used typically comprise a solvent and coloring ions.

Suitable solvents include water, alcohols (especially low-boiling alcohols, e.g. with a boiling point below about 100° C.) and ketons.

The solvent should be able to dissolve the coloring ions used.

Specific examples of solvents which can be used for dissolving the cations contained in the solution include water, methanol, ethanol, iso-propanol, n-propanol, butanol, acetone, ethylene glycol, glycerol and mixtures thereof.

The solvent is typically present in an amount sufficient to dissolve the components contained or added to the solvent.

Suitable coloring ions include the ions of V, Mn, Fe, Er, Tb, Y, Ce, Sm, Dy or combinations thereof. Besides those cations the solution may contain in addition coloring agent(s) selected from those listed in the Periodic Table of Elements (in the 18 columns form) and are classified as rare earth elements (including Ce, Nd, Sm, Eu, Gd, Dy, Ho, Tm, Yb and Lu) and/or of the subgroups of the rare earth elements and/or salts of transition metals of the groups 3, 4, 5, 6, 7, 9, 10, 11.

Anions which can be used include $OAc^-$, $NO_3^-$, $NO_2^-$, $CO_3^{2-}$, $HCO_3^-$, $ONC^-$, $SCN^-$, $SO_4^-$, $SO_3^{2-}$, gluturate, lactate, gluconate, propionate, butyrate, glucuronate, benzoate, phenolate, halogen anions (fluoride, chloride, bromide) and mixtures thereof.

The solution may also contain organic components. By adding organic molecules, the properties (e.g. viscosity, vapor pressure, surface tension, stability, etc) can be modified.

Organic components which can be added include PVA, PEG, ethylenglycol, surfactants or mixtures thereof.

The solution may also contain one or more complexing agent(s). Adding a complexing agent can be beneficial to improve the storage stability of the solution, accelerate the dissolving process of salts added to the solution and/or increase the amount of salts which can be dissolved in the solution.

The solution may also contain marker substance(s). Adding a marker substance(s) can be beneficial in order to enhance the visibility of the solution during use, especially, if the solution is transparent and color-less.

Examples of marker substance(s) which can be used include food colorants like Riboflavin (E101), Ponceau 4R (E124), Green S (E142).

Suitable coloring solutions are also described in WO 2004/110959 (3M), WO 00/46168 A1 (3M), WO 2008/098157 (3M), WO 2009/014903 (3M) and WO 2013/022612 (3M).

The coloring solution is typically applied to the surface of the porous 3-dim article with a suitable application device comprising a reservoir and an opening, the reservoir containing the coloring solution as described in the present text.

According to a particular embodiment, the device may have the shape of a pen, the pen comprising a housing, a brush tip, a removable cap and a reservoir for storing the solution described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the coloring solution and will help the practitioner to save time.

According to one embodiment, the process can be described as follows:

A process for producing a sintered lithium disilicate glass ceramic dental restoration out of a porous 3-dim article, the process comprising the step of
  a) providing a porous 3-dim article, the 3-dim article having the shape of a dental milling block, the porous 3-dim article having a density from 0.5 to 2 g/cm3,
  b) machining the porous 3-dim article to obtain a machined porous 3-dim article having the shape of a dental restoration with an outer and inner surface,
  c) optionally coloring the porous 3-dim article having the shape of a dental restoration,
  d) sintering the porous 3-dim article having the shape of a dental restoration with an outer and inner surface without supporting the inner surface of the porous 3-dim article having the shape of a dental restoration during sintering to obtain a sintered lithium disilicate ceramic dental restoration, the sintering preferably being done under reduced atmospheric pressure conditions, the sintered lithium disilicate glass ceramic dental restoration having a density from 2 to 3 g/cm3 and comprising
  Si oxide calculated as SiO2 from 55 to 80 wt.-%,
  Li oxide calculated as Li2O from 7 to 16 wt.-%,
  Al oxide calculated as Al2O3 from 1 to 5 wt.-%, and
  P oxide calculated as P2O5 from 1 to 5 wt.-%,
  wt.-% with respect to the weight of the dental restoration.

According to another embodiment, the process can be described as follows:

A process for producing a sintered lithium disilicate glass ceramic dental restoration out of a porous 3-dim article, the process comprising the step of
  producing a porous 3-dim article having the shape of a dental restoration with an outer and inner surface using a build-up technology, the porous 3-dim article having a density from 0.5 to 2 g/cm3,
  optionally coloring the porous 3-dim article having the shape of a dental restoration,
  sintering the porous 3-dim article having the shape of a dental restoration with an outer and inner surface without supporting the inner surface of the porous 3-dim article having the shape of a dental restoration during sintering to obtain a sintered lithium disilicate ceramic dental restoration,
  the sintering being done under reduced atmospheric pressure conditions, the reduced atmospheric pressure conditions being applied at a temperature above 600 or 700° C.,
  optionally sintering the porous dental restoration without using a support structure during sintering,
  the sintered lithium disilicate glass ceramic dental restoration having a density from 2 or 2.1 to 3 g/cm3 and comprising
  Si oxide calculated as SiO2 from 55 to 80 wt.-%,
  Li oxide calculated as Li2O from 7 to 16 wt.-%,
  Al oxide calculated as Al2O3 from 1 to 5 wt.-%, and
  P oxide calculated as P2O5 from 1 to 5 wt.-%,
  wt.-% with respect to the weight of the dental restoration.

According to a further embodiment the present invention is directed to a process for producing a sintered lithium disilicate glass ceramic dental restoration out of a porous 3-dim article, the process comprising the step of
  sintering the porous 3-dim article having the shape of a dental restoration with an outer and inner surface to obtain a sintered lithium disilicate ceramic dental restoration, the sintered lithium disilicate glass ceramic dental restoration comprising
  Si oxide calculated as SiO2 from 55 to 80 wt.-%,
  Li oxide calculated as Li2O from 7 to 16 wt.-%,
  Al oxide calculated as Al2O3 from 1 to 5 wt.-%, and
  P oxide calculated as P2O5 from 1 to 5 wt.-%,
  wt.-% with respect to the weight of the dental restoration,
the sintering of the porous 3-dim article having the shape of a dental restoration being conducted without supporting the inner surface of the dental restoration during sintering, wherein the description of the process conditions and formulations and shapes of the article are as described in the present text.

The invention is also directed to a kit of parts comprising a porous 3-dim article having the shape of a dental milling block, an instruction of use comprising the following process steps:
  machining a porous dental restoration out of the 3-dim porous article having the shape of a dental milling block,
  optionally coloring the porous dental restoration with a coloring solution,
  sintering the porous dental restoration, the sintering being done under reduced atmospheric pressure conditions, the reduced atmospheric pressure conditions being applied at least above a temperature of 600 or 700° C.,
the porous 3-dim article having a pore volume from 20 to 70 vol.-% and comprising the following oxides:
  Si oxide calculated as SiO2 from 55 to 80 wt.-%,
  Li oxide calculated as Li2O from 7 to 16 wt.-%,
  Al oxide calculated as Al2O3 from 1 to 5 wt.-%, and
  P oxide calculated as P2O5 from 1 to 5 wt.-%,
wt.-% with respect to the weight of the porous 3-dim article.

The porous 3-dim article, the dental milling block, the dental restoration, the coloring solution, the machining step, the coloring step, the sintering step and the other process conditions are as described in the present text above.

All components used for producing the dental restoration described in the present text should be sufficiently biocompatible either from the beginning or in its final state (e.g. due to incorporation in a matrix); that is, the composition should not produce a toxic, injurious, or immunological response in living tissue.

The dental restoration described in the present text does not contain components or additives which jeopardize the intended purpose to be achieved with the invention. Thus, components or additives added in an amount which finally results in a non-tooth-colored dental article after sintering are usually not contained. Typically, a dental article is characterized as not being tooth colored, if it cannot be allocated a color from the Vita™ color code system, known to the person skilled in the art. Additionally, components which will reduce the mechanical strength of the dental restoration to a degree, where mechanical failure will occur, are usually also not included in the dental article.

The process described in the present text does typically not comprise either or all of the following process steps:
  machining a sintered lithium disilicate 3-dim article;
  machining an article containing lithium metasilicate as main crystalline phase;
  machining an article containing lithium disilicate as main crystalline phase.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Measurements

Quantitative Rietveld Phase Analysis/Crystalline Content

If desired, a quantitative Rietveld phase analysis can be done with a Bruker (Germany) AXS Type: D8Discover spectrometer. Such an analysis allows e.g. the determination of the content of crystalline phases.

Flexural Strength

If desired, the flexural strength can be measured with a Zwick (Germany) type Z010 machine according to ISO 6872.

X-ray Opacity

If desired, x-ray opacity can be measured with an X-ray machine (60 kV; sample thickness: 2 mm) according to ISO 6872.

Coefficient of Thermal Extension (CTE)

If desired, CTE can be determined with a Netzsch (Germany) Type DIL 402 C dilatometer according to ISO 6872 (sample size: 4.5*4.5*26 mm; heating rate: 5.00 K/min).

If desired, the CTE value(s) can also be calculated similar to refractive indices by using additive factors as described in the literature known to the skilled person (e.g. Appen, A. A., Ber. Akad. Wiss. UDSSR 69 (1949), 841-844).

Chemical Stability

If desired, chemical stability can be tested according to ISO 6872. Test specimens having a surface of 30-40 cm$^2$; (50*30 mm; 1-4 mm thickness) are typically cut and stored for 18 h in 4% acetic acid (80° C.).

Translucency/Contrast Ratio (CR)

If desired, the translucency can be determined with a Macbath TD 932 System. Samples are cut into slices (thickness: 1.50+/−0.05 mm), polished (surface roughness: 9 μm) and the translucency is measured.

Milling Properties

If desired, milling experiments can be done on a Sirona, Cerec™ Inlab machine. Blocks from sample GK 79 (14× 12×18 mm) were pressed and an anterior crown was milled out of a porous presintered block (650° C./20 min). The porous presintered block could easily be milled.

Particle Size

If desired, the mean particle size can be determined using a commercially available granulometer (Laser Diffraction Particle Size Analysis Instrument, MASERSIZER 2000; Malvern Comp.) according to the instruction of use provided by the manufacturer.

Porosity

If desired, the porosity or open porosity can be measured using a mercury porosimeter in accordance with DIN 66133 as available under the designation "Poremaster 60-GT" from Quantachrome Inc., USA.

Density

If desired, the density can be determined by determining the weight and the dimension of the sample and calculating the density Example 1 (Non-Colored Lithium Disilicate Ceramic Disc)

The following amounts of powder were mixed in a bottle: 72.1 wt.-% SiO2, 15.1 wt.-% Li2CO3, 3.4 wt.-% Li3PO4, 3.5 wt.-% Al(OH)3, 3.2 wt.-% K2CO3 and 2.7 wt.-% ZrO2. In a next step the powder mixture was melted in a platinum crucible at 1500° C. and fritted in water. This was repeated three times. Afterwards the frit was milled. The resulting glass powder had the following particle size distribution: d50: 13.5 µm (d10: 2.5 µm, d90: 49.6 µm).

The powder was mixed with 10 wt.-% water and pressed to discs (dimensions: 20 mm×1.5 mm) or blocks (dimensions: 12 mm×14 mm×18 mm) by applying a pressure of 7.5 MPa).

Glass ceramic bodies with 98-100% theoretical density were achieved with the following one step crystallization and sintering program:
Heating with 5 K/min to 730° C.;
Holding at 730° C. till Vacuum on;
Heating with 10 K/min to 930° C.;
Holding time 10 min;
Cooling with 10 K/min to 730° C.;
Holding at 730° C. Vacuum off,
Cooling within furnace.

Figure 1:
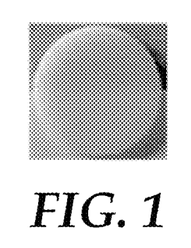
FIG. 1 shows a sample of a non-colored lithium disilicate ceramic disc.

Conducting these processing steps resulted in dense glass ceramic discs with the following properties:
Density: 2.43 g/cm3
Crystallinity: 54%
Bending strength: 250 MPa
Opacity: 55%.
The obtained sample is shown in FIG. 1.

Example 2 (Colored Lithium Disilicate Ceramic Disc)

A disc as described in Example 1 was prepared. The disc was pre-sintered at 550 to 650° C. to obtain a porous body.

The porous body was colored by immersing it in commercially available coloring liquids or by applying commercially available coloring liquids with a brush to its surface (Lava™ Plus Coloring Liquids and/or Lava™ Plus Effect Shades; 3M ESPE).

Figure 2:
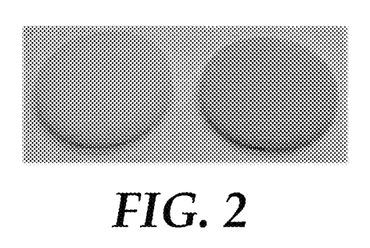
FIG. 2 shows a sample of a colored lithium disilicate ceramic disc.

After sintering, a colored lithium disilicate glass ceramic was obtained, which has been colored in the amorphous and porous state (i.e. before sintering). The sample obtained is shown in FIG. 2 on the right side. For comparison, the left disc is non-colored.

Example 3 (Dental Restorations)

Figure 3:
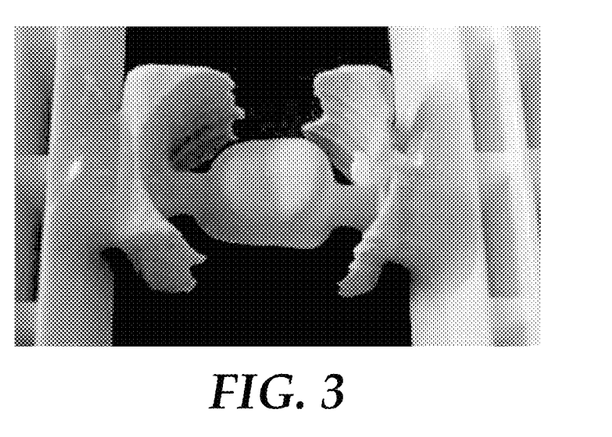
FIG. 3 shows crown machined from a dental milling block made of a pre-sintered lithium silicate material.

A crown was machined out of a pre-sintered dental milling block obtained as described in Example 1 using a Lava™ CNC 500 milling machine (3M ESPE). A picture of the crown machined from a dental milling block made of a pre-sintered lithium silicate material is shown in FIG. 3.

Similarly, an inlay was machined out of a pre-sintered block obtained as described in Example 1 using a Sirona CEREC™ inLab.

Figure 4:
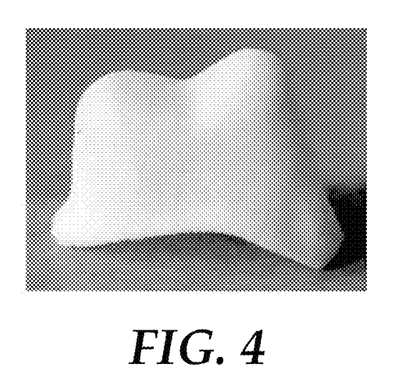
FIG. 4 shows a crown based on a lithium disilicate material.

In FIG. 4 a sintered lithium disilicate crown is shown. The crown was produced by machining it out of a pre-sintered block, coloring the obtained crown in a pre-sintered stage as described in Example 2 and sintering the crown in one step applying the conditions described in Example 1.

The crown was sintered without using a sintering support. The obtained sintered dental restoration did not show any relevant distortion.

Figure 5:
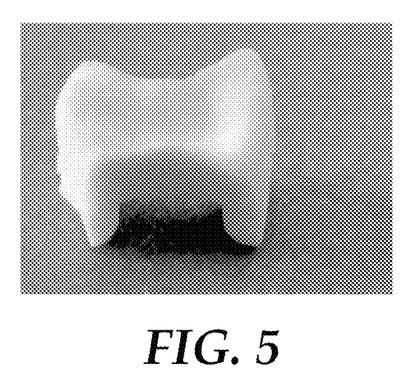
FIG. 5 shows an inlay based on a lithium disilicate material.

FIG. 5 shows an inlay produced in the same manner as the crown above.

Example 4 (Comparison)

An artificial tooth stump was provided, the surface of the tooth stump was scanned and a dental crown designed for that tooth stump using Lava™ Design 7 software 3M ESPE). One dental crown was machined out of a pre-sintered lithium disilicate block—Crown A. One dental crown was machined out of a pre-sintered Lava™ DVS block (3M ESPE)—Crown B. Crown A was sintered according to the process described in Example 1 without supporting the inner surface of the dental crown during sintering.

Crown B was sintered as described in the instruction of use provided by the manufacturer, but without supporting the inner surface of the dental crown during sintering.

Figure 6:
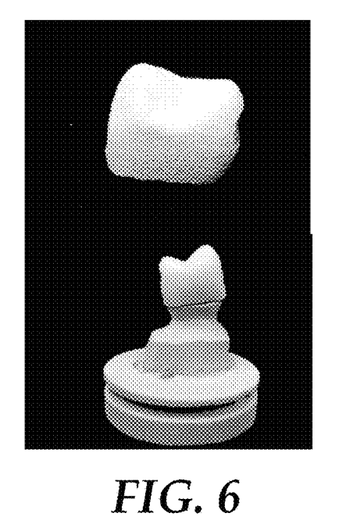
FIG. 6 shows a sintered crown according to the invention placed on an artificial tooth stump.
Figure 7:
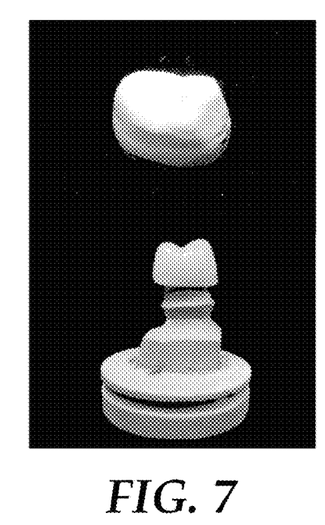
FIG. 7 shows a sintered crown according to the prior art placed on an artificial tooth stump.

The sintered crowns were placed on the artificial tooth stump and inspected visually for fit. The results are shown in FIGS. 6 and 7. Crown A fitted nearly perfectly on the artificial tooth stump (FIG. 6), whereas Crown B did not fit (FIG. 7).

Example 5 (Reduced Atmospheric Pressure Conditions)

Discs as described in Example 1 were prepared. Different conditions of heating rate and duration of vacuum were applied. The sintering temperature was 925° C. and the dwell time at this temperature was 600 s. The respective conditions are shown in Table 1.

TABLE 1

| Nr | Temperature range T1 during which reduced atmospheric pressure conditions were installed | Heating rate | Appearance (determined by inspecting with human eyes) |
|---|---|---|---|
| 1 | 730° C.-730° C. | 5K/min | Clear white, translucent (see FIG. 1) |
| 2 | 500° C.-500° C. | 5K/min | grayish |
| 3 | 450° C.-300° C. | 5K/min | grayish |
| 4 | 23° C.-23° C. | 5K/min | grayish |
| 5 | 23° C.-23° C. | 25K/min | more grayish |

It was found that a sufficiently translucent article can only be obtained when the reduced atmospheric pressure conditions are applied above a certain temperature range. Applying the reduced atmospheric pressure conditions already below a certain temperature resulted in articles having a grayish appearance.

Further the heating rate should be not too fast. It was found that a moderate heating rate (e.g. 2 to 10 K/min) may be further beneficial for achieving an aesthetic article.

Figure 8:
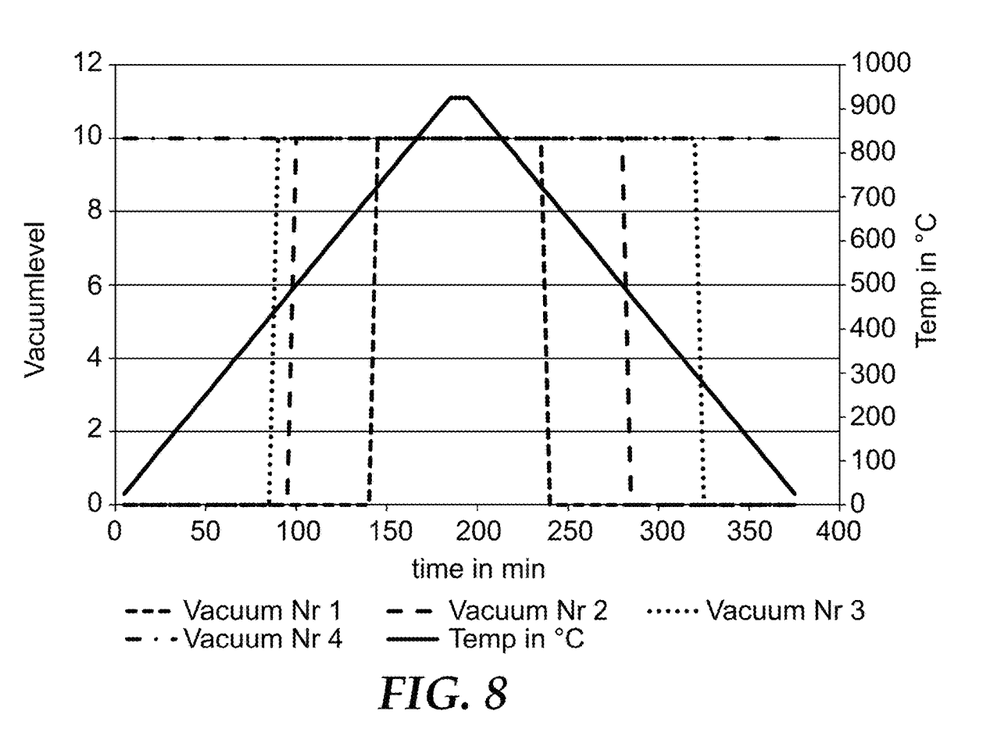
FIG. 8 shows a diagram containing suitable reduced atmospheric pressure and temperature conditions.

FIG. 8 visualizes the reduced pressure and temperature conditions applied in the Examples 1-4 described above. The level of vacuum corresponds to the levels which can be adjusted according to the instruction of use provided by the manufacturer. Level 0 means no vacuum (i.e. ambient conditions); level 10 means maximum vacuum possible.

Example 6 (Additive Manufacturing)

If desired, a porous 3-dim article having the shape of a dental restoration can also be produced by applying an additive manufacturing technology, e.g. using a 3d-printing technique. A suitable process can be described as follows: An STL computer file describing the 3-dim. shape of the dental restoration to be produced (e.g. dental veneer) is loaded into the software of the printer (ZCorp 310 plus printer; ZCorporation, Burlington, USA).

The printing is done as described in the instruction for use provided by the manufacturer of the printer, wherein parameters like shrinkage and layer thickness are additionally taken into account.

A water based binder (obtainable from ZCorporation, Burlington, USA) is jetted onto specific sections of the uppermost layer of the powder as calculated by the software of the printer. The binder component on the surface of the powder is partly dissolved. The respective particles will stick together. This step is repeated until the shape of the desired article is obtained. After drying, the printed article is removed from the powder-bed and excessive powder is removed (e.g. using pressurized air).

The invention claimed is:

1. A process for producing a sintered lithium disilicate glass ceramic dental restoration out of a porous 3-dim article, the process comprising:
   sintering the porous 3-dim article having the shape of a dental restoration with an outer and inner surface to obtain a sintered lithium disilicate ceramic dental restoration,
   the sintered lithium disilicate glass ceramic dental restoration comprising:
   Si oxide calculated as SiO2: from 55 to 80 wt.-%;
   Li oxide calculated as Li2O: from 7 to 16 wt.-%;
   Al oxide calculated as $Al_2O_3$: from 1 to 5 wt.-%; and
   P oxide calculated as $P_2O_5$: from 1 to 5 wt.-%,
   wt.-% with respect to the weight of the dental restoration,
   the sintering being done under reduced atmospheric pressure conditions, the reduced atmospheric pressure conditions being first applied at a temperature of at least 600° C.

2. The process of claim 1 comprising:
   providing a porous 3-dim article, the 3-dim article having either the shape of a dental milling block or of a dental restoration with an outer and inner surface; and
   for porous 3-dim articles having the shape of a milling block, machining the porous 3-dim article to obtain a machined porous 3-dim article having the shape of a dental restoration with an outer and inner surface.

3. The process of claim 1, the porous 3-dim article having the shape of a dental crown, dental bridge, veneer, inlay, onlay or part thereof.

4. The process of claim 1, the porous 3-dim article being characterized by at least one of the following features:
   Pore volume: 70 to 20%;
   Density: from 0.5 to 2 g/cm3;
   Flexural strength: 20 to 75 MPa according to ISO 6872.

5. The process of claim 1, the material of the sintered lithium disilicate glass ceramic dental restoration being characterized by at least one of the following features:
   Pore volume: 0 to 2%;
   Density: from 2.1 to 3 g/cm3;
   Flexural strength: 250 to 450 MPa according to ISO 6872.

6. The process of claim 1, the porous 3-dim article being obtained by a process comprising an additive manufacturing technology using a glass powder, the process optionally comprising the step of coloring the porous 3-dim article by using coloring components during the additive manufacturing technology.

7. The process of claim 1, the porous 3-dim article being obtained by a process comprising the steps of:
   providing a glass powder;
   pressing the glass powder to obtain a 3-dim article; and
   conducting a pre-sintering step to obtain the porous 3-dim article.

8. The process of claim 1, further comprising a coloring step, the coloring step being conducted by:
   either applying a coloring solution to only parts of the outer surface of the porous 3-dim article having the shape of a dental restoration; or
   treating the whole surface of the porous 3-dim article having the shape of a dental restoration with a coloring solution.

9. The process of claim 8, the coloring solution comprising a solvent and coloring ions selected from V, Mn, Fe, Er, Tb, Y, Ce, Sm, Dy or combinations thereof or coloring pigments comprising any of those coloring ions or combinations thereof.

10. The process of claim 1, the sintered lithium disilicate glass ceramic dental restoration further comprising at least one, two, three or all of the following components:
    K oxide calculated as K2O: from 0.1 to 5 wt.-%;
    Zr oxide calculated as $ZrO_2$: from 0.1 to 15 wt.-%;
    Zn oxide calculated as ZnO2: from 0 to 2 wt.-%;
    Ce oxide calculated as CeO2: from 0 to 2 wt.-%;
    Cs oxide calculated as CsO2: from 0 to 8 wt.-%;
    Coloring metal oxides calculated as MO2 or M2O3, with M being a metal ion: from 0 to 5 wt.-%.

11. The process of claim 1, the lithium disilicate glass ceramic dental restoration not comprising ZrO2 in an amount of more than 20 wt.-%.

12. The process of claim 1, the process not comprising at least one or all of the following steps:
    machining the sintered lithium disilicate 3-dim article;
    machining an article containing lithium metasilicate as main crystalline phase;
    machining an article containing lithium disilicate as main crystalline phase.

13. The process of claim 1, wherein the sintering is conducted without supporting the inner surface of the dental restoration.

14. A process for producing a sintered lithium disilicate glass ceramic dental restoration out of a porous 3-dim article, the process comprising:
    providing a porous 3-dim article, the 3-dim article having the shape of a dental milling block, the porous 3-dim article having a density from 0.5 to 2 g/cm3,
    machining the porous 3-dim article to obtain a machined porous 3-dim article having the shape of a dental restoration with an outer and inner surface,
    optionally coloring the porous 3-dim article having the shape of a dental restoration,
    sintering the porous 3-dim article having the shape of a dental restoration with an outer and inner surface at reduced atmospheric pressure without supporting the inner surface of the porous 3-dim article having the shape of a dental restoration during sintering to obtain a sintered lithium disilicate ceramic dental restoration,
    the sintering being done under reduced atmospheric pressure conditions, the reduce atmospheric pressure conditions being first applied at a temperature above 600° C.,
    the sintered lithium disilicate glass ceramic dental restoration having a density from 2 to 3 g/cm3 and comprising:
    Si oxide calculated as SiO2: from 55 to 80 wt.-%;
    Li oxide calculated as Li2O: from 7 to 16 wt.-%;
    Al oxide calculated as $Al_2O_3$: from 1 to 5 wt.-%; and
    P oxide calculated as $P_2O_5$: from 1 to 5 wt.-%,
    wt.-% with respect to the weight of the dental restoration.

* * * * *